United States Patent [19]

Schmidt et al.

[11] 4,408,044

[45] Oct. 4, 1983

[54] PREPARATION OF 3,6-DISUBSTITUTED 4-AMINO-1,2,4-TRIAZIN-5-ONES

[75] Inventors: Thomas Schmidt, Haan; Helmut Timmler, Wuppertal; Gerhard Bonse, Cologne; Heinz U. Blank, Odenthal; Gerhard Marzolph, Cologne, all of Fed. Rep. of Germany

[73] Assignee: Bayer Aktiengesellschaft, Leverkusen, Fed. Rep. of Germany

[21] Appl. No.: 338,811

[22] Filed: Jan. 11, 1982

[30] Foreign Application Priority Data

Jan. 24, 1981 [DE] Fed. Rep. of Germany ....... 3102318

[51] Int. Cl.³ .......................................... C07D 253/06
[52] U.S. Cl. ................................................... 544/182
[58] Field of Search ............................................. 544/182

[56] References Cited

U.S. PATENT DOCUMENTS

| 4,175,188 | 11/1979 | Klenk et al. | 544/182 |
| 4,309,538 | 1/1982 | Schmidt et al. | 544/182 |
| 4,315,094 | 2/1982 | Bonse et al. | 544/182 |
| 4,326,056 | 4/1982 | Kleemann et al. | 544/182 |

FOREIGN PATENT DOCUMENTS

| 2165554 | 7/1973 | Fed. Rep. of Germany . |
| 2556835 | 6/1977 | Fed. Rep. of Germany . |
| 2856750 | 7/1980 | Fed. Rep. of Germany . |
| 1368416 | 9/1974 | United Kingdom . |
| 1560398 | 2/1980 | United Kingdom . |

Primary Examiner—John M. Ford
Attorney, Agent, or Firm—Sprung, Horn, Kramer & Woods

[57] ABSTRACT

The herbicidal 3,6-substituted 4-amino-1,2,4-triazin-5-one of the general formula

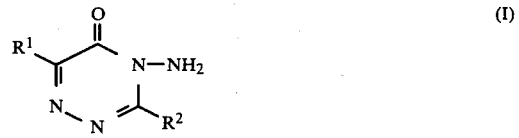

wherein
$R^1$ and $R^2$ have the meaning given in the description,
is obtained in good yields by a new two-stage cyclization reaction if an α-ketocarboxylic acid amide of the general formula

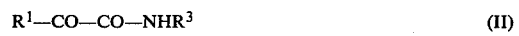

$$R^1-CO-CO-NHR^3 \qquad (II)$$

is reacted with a hydrazidine of the general formula

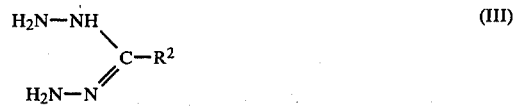

if appropriate in the presence of a diluent at temperatures between 0° and 150° C., whereby in the first process stage a condensation reaction takes place to give condensation products which still have open chains, and in the second process stage an elimination reaction with ring closure takes place to give the end product of formula (I).

12 Claims, No Drawings

PREPARATION OF 3,6-DISUBSTITUTED 4-AMINO-1,2,4-TRIAZIN-5-ONES

The present invention relates to an unobvious process for the preparation of certain largely known herbicidal 3,6-disubstituted 4-amino-1,2,4-triazin-5-ones.

It has already been disclosed that certain 1,2,4-triazin-5-ones are obtained if α-ketocarboxylic acids, or esters or nitriles thereof, are reacted with hydrazines or salts thereof in the presence of a solvent and, if appropriate, in the presence of an acid-binding agent at a temperature between −10° and +100° C., according to the following equation (see DE-OS'en (German Published Specifications) Nos. 2,224,161 and 2,556,835):

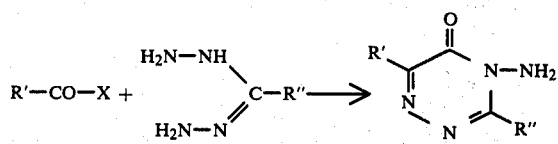

in which

R' denotes a hydrogen atom or an alkyl, cycloalkyl, aralkyl, aryl, thienyl or furyl radical, R'' denotes an alkyl, cycloalkyl, aralkyl or aryl radical, X denotes —COOH, —COOR''', or —CN; and R''' denotes an alkyl, aralkyl or aryl radical.

However, this process has the disadvantage that the nitriles (i.e. compounds in which X denotes CN), if they react at all, can only be reacted with very poor yields, and the acids or esters (i.e. compounds in which X denotes —COOH or —COOR''') normally have to be prepared from the nitriles by hydrolysis or alcoholysis, in a multistage reaction, via the stage of the amide.

The present invention now provides a process for the production of a 3,6-disubstituted 4-amino-1,2,4-triazin-5-one of the general formula

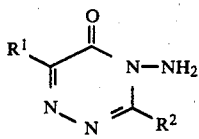

(I)

in which $R^1$ represents a hydrogen atom or an optionally substituted alkyl, optionally substituted cycloalkyl, optionally substituted cycloalkenyl, alkenyl, furyl, thienyl, optionally substituted aryl or optionally substituted aralkyl radical, and $R^2$ represents an alkyl, optionally substituted cycloalkyl, optionally substituted aryl or optionally substituted aralkyl radical, characterized in that an α-ketocarboxylic acid amide of the general formula $$R^1-CO-CO-NHR^3 \quad (II)$$

in which $R^1$ has the meaning given above and $R^3$ represents a hydrogen atom or a group of the general formula —CO—$R^4$, wherein $R^4$ represents an alkyl, cycloalkyl, optionally substituted aryl or optionally substituted aralkyl radical, is reacted with a hydrazidine of the general formula

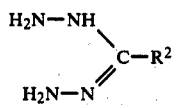

(III)

in which $R^2$ has the meaning given above, or, preferably, an acid addition salt thereof, if appropriate in the presence of a diluent at a temperature between about 0° and 150° C., in two process stages, whereby in the first process stage a condensation reaction takes place to give condensation products which still have open chains, and in the second process stage an elimination reaction with ring closure takes place to give the end product of formula (I).

It is surprising that the two-stage cyclization reaction of the present invention allows the generally known 3,6-disubstituted 4-amino-1,2,4-triazin-5-ones of the formula (I) to be prepared in very good yields and in very pure form.

The first process stage (condensation reaction) is carried out, if appropriate, in the presence of an acid catalyst, and the second process stage (elimination reaction with ring closure) is carried out, if appropriate, in the presence of a base, preferably without intermediate isolation of the condensation products of the general formula

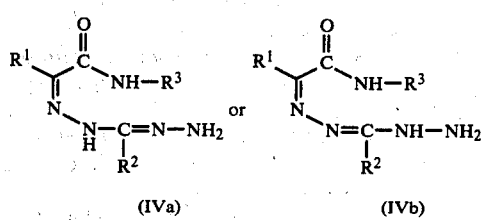

which are formed in the first process stage.

It is decidedly surprising that the amides of the formula (II), which are inert to reaction in comparison to the ketocarboxylic acids or the esters thereof, can be reacted very easily and in high yield in the manner indicated.

The process according to the invention has a number of advantages. In particular, the α-ketocarboxylic acid amides of the formula (II), which are to be used as starting materials, can easily be prepared in high yield and purity directly from the corresponding nitriles. In addition, the process according to the invention is widely applicable and leads to hardly any formation of by-products. It is particularly advantageous to carry out the whole reaction as a "one-pot process".

3,6-disubstituted 4-amino-1,2,4-triazin-5-ones of formula (I) are preferably prepared by the process according to the invention are those in which, $R^1$ represents a hydrogen atom, an optionally substituted straight-chain or branched alkyl radical having 1 to 12 carbon atoms (the substituent(s) being selected, for example, from halogen-particularly fluorine and chlorine, and alkoxy and alkylthio, each having 1 to 4 carbon atoms), an optionally substituted cycloalkyl radical having 3 to 6 carbon atoms or an optionally substituted cycloalkenyl radical having 4 to 6 carbon atoms (the substituent(s) being selected, for example from halogen-particularly fluorine and chlorine, and alkyl and alkoxy, each having 1 to 4 carbon atoms, and phenyl which is optionally substituted by halogen-particularly fluorine, chlorine and bromine, and alkyl having 1 to 4 carbon atoms), an alkenyl radical having 2 to 6 carbon atoms, a furyl or thienyl radical, an optionally substituted aryl or aralkyl radical, each having 6 to 10 carbon atoms in the aryl part and 1 or 2 carbon atoms in the alkyl part (such as, in particular, phenyl and benzyl, the substituent(s) preferably being selected from halogen [particularly fluorine, chlorine and bromine], alkyl, alkoxy and alkylthio, each having 1 to 4 carbon atoms, halogenoalkyl, halogenoalkoxy and halogenoalkylthio, each having 1 to 4 carbon atoms and up to 5 identical or different halogen atoms—such as, in particular, fluorine and chlorine atoms, and nitro), and $R^2$ represents a straight-chain or branched alkyl radical having 1 to 6 carbon atoms, an optionally substituted cycloalkyl having 3 to 6 carbon atoms (the preferred substituent(s) being selected from those mentioned in this respect in the case of $R^1$), and an optionally substituted aryl or aralkyl radical, each having 6 to 10 carbon atoms in the aryl part and 1 or 2 carbon atoms in the alkyl part (such as, in particular, phenyl and benzyl, the preferred substituent(s) being selected from those mentioned in this respect in the case of $R^1$).

Those compounds of the formula (I) are particularly preferred, in which $R^1$ represents an isopropyl, sec.-butyl, n-butyl, tert.-butyl, sec.-pentyl, neopentyl, 1,1-dimethylpropyl, dichlorocyclopropyl, methyldichlorocyclopropyl, cyclobutyl, cyclopentyl, cyclohexyl, furyl, or thienyl radical or a phenyl radical which is optionally substituted by fluorine, chlorine, bromine, methoxy, nitro, methyl and trifluoromethyl, and $R^2$ represents a methyl, ethyl, n-propyl, isopropyl, n-butyl, sec.-butyl, tert.-butyl, cyclopropyl, cyclobutyl or cyclopentyl radical.

If, for example, phenylglyoxylic acid amide and acethydrazidine hydrochloride are used as starting materials, the course of the reaction according to the invention is illustrated by the following summarizing equation:

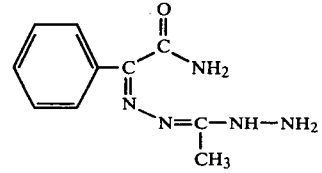

In this reaction, the following compounds occur as intermediate products:

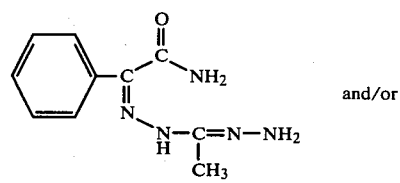
and/or
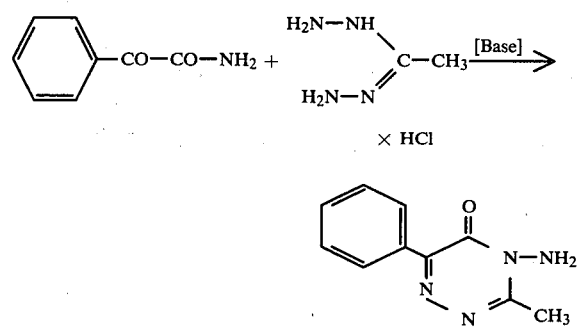

Preferred α-ketocarboxylic acid amides of formula (II) which are required as starting materials in carrying out the process according to the invention are those in which $R^1$ represents those radicals which have already been mentioned for these substituents in connection with the description of the preferred and particular preferred substances of the formula (I) which can be prepared according to the invention, and $R^3$ represents a hydrogen atom or a group of the general formula —CO—$R^4$, wherein $R^4$ preferably represents an alkyl radical having 1 to 10 carbon atoms, a cycloalkyl having 3 to 6 carbon atoms or an optionally substituted aryl or aralkyl radical, each having 6 to 10 carbon atoms in the aryl part and 1 or 2 carbon atoms in the alkyl part, (such as, in particular, phenyl and benzyl, the substituent(s) being selected from those mentioned for such radicals in the case of $R^1$).

α-Ketocarboxylic acid amides of the formula (II) are known (see, for example, Beilstein 10, 658; 10/I, 314; 10/II, 456 and 3, 620) and are the subject of U.S. application Ser. No. 227,442 filed Jan. 22, 1981, allowed, and U.S. application Ser. No. 235,497 filed Feb. 19, 1981, now pending. They can be prepared, for example, by partial hydrolysis of appropriate nitrile derivatives, if appropriate under acylating conditions (also see the examples hereinbelow).

The following may be individually mentioned as examples of compounds of formula (II): phenylglyoxylic acid amide, trimethylpyruvic acid amide, phenylglyoxylic acid N-acetyl-amide, trimethylpyruvic acid N-acetyl-amide, cyclohexylglyoxylic acid amide, cyclohexylglyoxylic acid N-acetyl-amide, dichlorocyclopropylglyoxylic acid amide and dichlorocyclopropylglyoxylic acid N-acetyl-amide.

Preferred hydrazidines of formula (III) which are additionally required as starting materials in carrying out the process according to the invention are those in which $R^2$ represents those radicals which have already been mentioned for these substituents in connection with the description of the preferred and particularly preferred substances of formula (I) which can be prepared according to the invention.

As already mentioned, the hydrazidines of the formula (III) are preferably employed in the form of inorganic or organic acid addition salts. Any of the strong inorganic and organic acids which can customarily be used are suitable as the acid component. The following may be mentioned as examples: hydrochloric acid, hydrobromic acid, nitric acid, sulphuric acid, p-toluenesulphonic acid, phosphoric acid, methanesulphonic acid and naphthalenedisulphonic acid.

The hydrazidines of the formula (III) and their acid addition salts are generally known compounds in organic chemistry, and they can be obtained in a generally known manner (in this context, see for example Liebigs Ann. Chem. 1975, pages 1120–1123 and Monatshefte Chem. 63, pages 285–300 (1933)). The following may be mentioned as examples: acethydrazidine, propionylhydrazidine, n-butylhydrazidine, isopropionylhydrazidine and cyclopropanecarboxylic acid hydrazidine, and hydrochlorides thereof.

Water as well as inert organic solvents are suitable diluents for the reaction according to the invention. These solvents preferably include the following compounds: ethers (such as tetrahydrofuran, dioxane or ethylene glycol monomethyl ether), amides (such as dimethylformamide, diethylformamide, dimethylacetamide or N-methylpyrrolidone), alcohols (such as methanol, ethanol, n-butanol, isobutanol, tert.-butanol, glycol, glycerine, n-propanol, ispropanol, amyl alcohol, cyclohexanol, 2-methyl-4-pentanol, methylglycol, n-hexanol, isohexyl alcohol, isoheptyl alcohol, n-heptanol, nonyl alcohol, dodecyl alcohol or methylcyclohexanol), hydrocarbons (such as benzene or toluene), and halogenated hydrocarbons (such as methylene chloride, chloroform, carbon tetrachloride, 1,2-dichloroethane, 1,1,2-trichloroethane, trichloroethylene and chlorobenzene). Appropriate mixtures of solvents can also be used.

The first stage of the process according to the invention can be advantageously carried out in the presence of an acid catalyst, this catalyst being employed, in general, in quantities of about 0.05 to 0.1 mol per mol of starting compound of formula (II). This is to be recommended particularly in the cases in which the less reactive N-substituted α-ketocarboxylic acid amides, and not the relatively reactive α-ketocarboxylic acid N-acylamides, are employed as starting materials. p-Toluenesulphonic acid has proved particularly suitable as the acid catalyst.

If the hydrazidines of formula (III) are employed in the form of acid addition salts as starting materials, the second stage of the process according to the invention must then be carried out in the presence of at least a stoichiometric quantity of a base. However, even in the case in which the hydrazidines are used in the free form, it can be advantageous to carry out the reaction in this stage with the addition of a catalytic quantity of a base. In principle, any of the customary inorganic and organic basic compounds which can be used as acid-binding agents can be employed as bases. These preferably include alkali metal and alkaline earth metal oxides, hydroxides, carbonates and bicarbonates (and the following are preferred as suitable metals: sodium, potassium and calcium) and tertiary amines (such as trimethylamine, triethylamine, pyridine, lauryldimethylamine, stearyldimethylamine, N,N-diethylcyclohexylamine, N-ethylpiperidine, N-methylpyrrolidine, α-, β- and γ-picoline, N-propylpiperidine, quinoline, isoquinoline, quinoxaline, tri-n-amylamine, tri-n-propylamine or N,N-dimethylbenzylamine).

In carrying out the process according to the invention, the reaction temperatures can be varied within a wide range. In general, the reaction is carried out at a temperature between 0° and +150° C., preferably between 10° and 120° C.

The reaction according to the invention can be continuously or discontinuously carried out under normal pressure or at elevated pressure.

In carrying out the process according to the invention, 1 to 1.5 mols, preferably 1 to 1.3 mols, of a hydrazidine of the formula (III) or an appropriate hydrazidine acid addition salt, and in the first process stage, if appropriate, 0.05 to 0.1 mol of an acid catalyst and in the second process stage, if appropriate, 1 to 3.5 mols of a base, are employed, in general, per mol of α-ketocarboxylic acid amide of the formula (II).

The isolation of the end product of the formula (I) is effected in a customary manner. It is possible, in addition, to isolate in a customary manner the stable intermediate stage (condensation product) of the formula

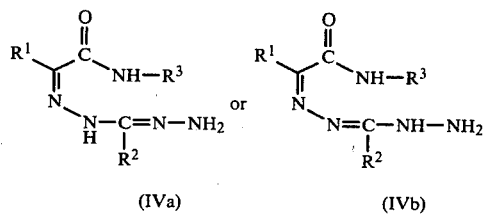

in which

R$^1$, R$^2$ and R$^3$ have the meaning given above, which intermediate stage occurs in the first step of the reaction according to the invention. In addition, the new compounds of the formula (IVa) or (IVb) can be present in several geometrical isomers of the syn and anti forms. In all cases, however, the end products of the formula (I) are formed in the second process stage.

The examples which follow serve to illustrate the invention in more detail.

PREPARATIVE EXAMPLES

EXAMPLE 1

(a) $(CH_3)_3C-CO-CO-NH_2$ 111.0 g (1 mol) of pivaloyl cyanide were added dropwise at room temperature to 800 g of a 36% strength solution of hydrogen bromide in glacial acetic acid, while stirring. After the addition had ended, the mixture was further stirred for 3 hours at room temperature. 9 ml (0.5 mol) of water were thereafter added dropwise to the mixture at 20° to 25° C., and the latter was further stirred for 1 hour at room temperature. The reaction solution was then poured into an excess of saturated sodium bicarbonate solution. The mixture was extracted three times with 200 ml of methylene chloride. The combined organic phases were washed with 200 ml of water, dried over sodium sulphate and concentrated by distilling off the solvent in vacuo. The residual oil crystallized throughout after some time. After recrystallization from petroleum ether, 113.5 g (88% of theory) of trimethylpyruvic acid amide of melting point 69° to 70° C. were obtained.

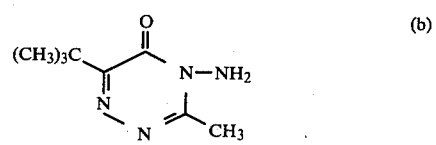
(b)

1 g of p-toluenesulphonic acid was added to 12.9 g (0.1 mol) of trimethylpyruvic acid amide, 1,000 ml of toluene and 16 g (0.13 mol) of acetyldrazidine hydrochloride, and the mixture was heated under reflux for 12 hours. 10 g of anhydrous, ground potassium carbonate were thereafter added to the mixture, and the latter was heated under reflux for a further 4 hours. The solution was filtered while hot, the filtrate was concentrated in vacuo and the product was crystallized out with the addition of 20 ml of petroleum ether. After the mixture had been filtered and the residue dried at 80° C. in vacuo, 12.2 g (67% of theory) of 4-amino-6-tert.-butyl-3-methyl-1,2,4-triazin-5-one of melting point 156° C. were obtained. The melting point of a sample purified by recrystallization (from benzene) was 161° to 163° C.

EXAMPLE 2

(a) $(CH_3)_3C-CO-CO-NH-CO-CH_3$

Firstly 25.6 g (0.25 mol) of acetic anhydride and then 27.8 g (0.25 mol) of pivaloyl cyanide were introduced, in each case at room temperature, into 49.0 g (0.5 mol) of initially introduced concentrated sulphuric acid. After the reaction mixture had been further stirred for 4 hours, 150 g of ice-water were added to it and it was thoroughly stirred. The precipitated reaction product was filtered off under suction, washed with 100 ml of water and dried. 37.0 g (86.5% of theory) of trimethylpyruvic acid N-acetylamide were obtained as colorless shiny platelets of melting point 82° to 84° C.

(b) A mixture of 17.1 g (0.1 mol) of trimethylpyruvic acid N-acetylamide, 12.5 g (0.1 mol) of acethydrazidine hydrochloride and 160 ml of methanol was stirred for 1 hour at room temperature and concentrated. The residue was stirred with 100 ml of pyridine for 2 hours at 50° C. and concentrated by evaporation. After recrystallization from ethanol, 15.8 g (87% of theory) of 4-amino-6-tert.-butyl-3-methyl-1,2,4-triazin-5-one of melting point 161° to 163° C. were obtained.

EXAMPLE 3

15 g (0.12 mol) of acethydrazidine hydrochloride were suspended in 100 ml of water and 17.1 g (0.1 mol) of trimethylpyruvic acid N-acetylamide were then added to the suspension. The mixture was stirred for 4 hours at 50° C., and the acid solution was rendered alkaline with 25% strength ammonia solution. The precipitated product was filtered off under suction at 20° C. and was washed with water. 14.3 g (78% of theory) of 4-amino-6-tert.-butyl-3-methyl-1,2,4-triazin-5-one were obtained as shiny white platelets of melting point 155° to 157° C.

EXAMPLE 4

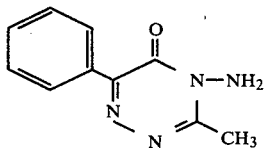

(a) 0.1 g of p-toluenesulphonic acid were added to 1.5 g (0.01 mol) of phenylglyoxylic acid amide, 1.3 g (0.01 mol) of acethydrazidine hydrochloride and 100 ml of toluene, and the mixture was heated to reflux for 12 hours, while stirring. 10 g of anhydrous, ground potassium carbonate were then added to the mixture, and the latter was heated under reflux for a further 4 hours. The mixture was thereafter filtered while hot, and the product was crystallized out by cooling the filtrate and was dried at 80° C. 1.8 g (89% of theory) of 4-amino-3-methyl-6-phenyl-1,2,4-triazin-5-one of melting point 158° to 161° C. were obtained.

EXAMPLE 5

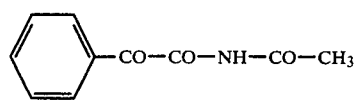 (a)

If the reaction was carried out analogously to the "Preparation of the starting material" of Example 1(b), and benzoyl cyanide was employed instead of pivaloyl cyanide, 38.5 g (79.5% of theory) of phenylglyoxylic acid N-acetylamide were obtained as colorless crystals of melting point 124° to 125° C.

(b) 19.1 g of phenylglyoxylic acid N-acetylamide (0.1 mol), 12.5 g (0.1 mol) of acethydrazidine hydrochloride and 160 ml of methanol were stirred for 1 hour at room temperature. The methanol was evaporated off, and the residue was stirred with 100 ml of pyridine for 2 hours at 50° C. The mixture was concentrated and the residue was stirred with water. The undissolved material was recrystallized from methanol. 17.9 g (88.6% of theory) of 4-amino-3-methyl-6-phenyl-1,2,4-triazin-5-one of melting point 165° to 167° C. were obtained.

EXAMPLE 6

15 g (0.12 mol) of acethydrazidine hydrochloride were suspended in 100 ml of water, and 19.1 g (0.1 mol) of phenylglyoxylic acid N-acetylamide were then added to the suspension. The suspension was stirred for 4 hours at 80° C., was rendered alkaline with 25% strength ammonia solution, and was filtered off under suction at 20° C. 16.8 g (83% of theory) of 4-amino-3-methyl-6-phenyl-1,2,4-triazin-5-one of melting point 166° to 168° C. were obtained.

The following compounds of the general formula

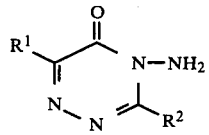 (I)

could be prepared in a corresponding manner and according to the process descriptions given:

TABLE 1

| Compound No. | $R^1$ | $R^2$ | Melting point (°C.) |
|---|---|---|---|
| 3 | H₃C—⌬— | CH₃ | 107 |
| 4 | H—⌬— | CH₃ | 110 |
| 5 | CF₃—⌬— | CH₃ | 169 |

TABLE 1-continued

| Compound No. | R¹ | R² | Melting point (°C.) |
|---|---|---|---|
| 6 | ![F-phenyl] | CH₃ | 137 |
| 7 | F-phenyl (para) | CH₃ | 163 |
| 8 | O₂N-phenyl | CH₃ | 233 |
| 9 | thienyl | CH₃ | 210 |
| 10 | furyl | CH₃ | 247 |
| 11 | Cl-phenyl | C₂H₅ | 156 |
| 12 | CH₃O-phenyl | C₂H₅ | 133 |
| 13 | cyclohexyl (H) | C₂H₅ | 114 |
| 14 | Br-phenyl | C₂H₅ | 158 |
| 15 | C₃H₇—iso | C₃H₇—n | 96 |
| 16 | phenyl | C₃H₇—n | 106 |
| 17 | Cl-phenyl | C₄H₉—tert | 153 |
| 18 | phenyl | 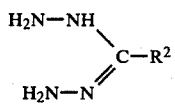 | 121 |
| 19 | C(CH₃)₃ | 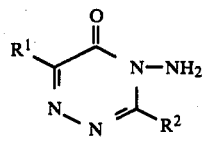 | 110 |
| 20 | C(CH₃)₃ | —C₂H₅ | 96 |

It will be appreciated that the instant specification and examples are set forth by way of illustration and not limitation, and that various modifications and changes may be made without departing from the spirit and scope of the present invention.

We claim:

1. A process for the production of a 3,6-disubstituted 4-amino-1,2,4-triazin-5-one of the formula

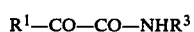

in which

R¹ is hydrogen, an alkyl radical having 1 to 12 carbon atoms, cycloalkyl radical having 3 to 6 carbon atoms or a cycloalkenyl radical having 4 to 6 carbon atoms, an alkenyl radical having 2 to 6 carbon atoms, a furyl or thienyl radical, or an aryl or aralkyl radical having 6 to 10 carbon atoms in the aryl part and 1 or 2 carbon atoms in the alkyl part, and R² is an alkyl radical having 1 to 6 carbon atoms, cycloalkyl having 3 to 6 carbon atoms, and an aryl or aralkyl radical having 6 to 10 carbon atoms in the aryl part and 1 or 2 carbon atoms in the alkyl part, comprising in two stages reacting an α-ketocarboxylic acid amide of the formula $$R^1-CO-CO-NHR^3$$

in which

R³ is hydrogen, or a group of the formula —CO—R⁴, and

R⁴ is an alkyl, cycloalkyl, optionally substituted aryl or optionally substituted aralkyl radical, with a hydrazidine of the formula $$\begin{array}{c} H_2N-NH \\ \phantom{H_2N-N}\diagdown \\ \phantom{H_2N-NNNN}C-R^2 \\ \phantom{H_2N-N}\diagup \\ H_2N-N \end{array}$$

or an acid addition salt thereof, in the first process stage a condensation reaction taking place to give condensation products which still have open chains, and in the second process stage an elimination reaction with ring closure taking place to give the desired end product.

2. A process according to claim 1, wherein the first process stage is carried out in the presence of an acid catalyst.

3. A process according to claim 2, wherein the acid catalyst is p-toluenesulphonic acid.

4. A process according to claim 1, wherein the second process stage is carried out in the presence of a base.

5. A process according to claim 1, wherein the second process stage is carried out without intermediate isolation of the condensation products formed in the first process stage.

6. A process according to claim 1, wherein the reaction is carried out in the presence of a diluent.

7. A process according to claim 1 wherein the reaction is carried out at a temperature between about 0° and 150° C.

8. A process according to claim 1 wherein the reaction is carried out at a temperature between about 10° and 120° C.

9. A process according to claim 1, wherein in the first stage about 1 to 1.5 mols of the hydrazidine or an acid addition salt thereof are employed per mol of α-ketocarboxylic acid amide.

10. A process according to claim 1, wherein about 0.05 to 0.1 mol of an acid catalyst per mol of α-ketocarboxylic acid amide is present during the first stage.

11. A process according to claim 1, wherein about 1 to 1.5 mols of an acid addition salt of the hydrazide are employed in the first stage and about 1 to 3.5 mols of a base are added in the second stage, molar amounts being calculated per mol of α-ketocarboxylic acid amide.

12. A process according to claim 1, in which
$R^1$ is an isopropyl, sec.-butyl, n-butyl, tert.-butyl, sec.-pentyl, neopentyl, 1,1-dimethylpropyl, dichlorocyclopropyl, methyldichlorocyclopropyl, cyclobutyl, cyclopentyl, cyclohexyl, furyl or thienyl radical, or a phenyl radical which is optionally substituted by fluorine, chlorine, bromine, methoxy, nitro, methyl or trifluoromethyl, and
$R^2$ is a methyl, ethyl, n-propyl, isopropyl, n-butyl, sec.-butyl, tert.-butyl, cyclopropyl, cyclobutyl or cyclopentyl radical.

* * * * *